United States Patent
Lauscher et al.

(10) Patent No.: US 6,365,136 B1
(45) Date of Patent: Apr. 2, 2002

(54) COMPOSITIONS FOR REMOVING OR LIGHTENING HAIR COLOR

(75) Inventors: Dirk Lauscher, Ober-Ramstadt; Herbert Deutz, Zwingenberg; Gabriele Hess, Erzhausen; Helga Kreher; Petra Braun, both of Muenster; Joerg Schmidt, Neu-Isenburg, all of (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/497,581

(22) Filed: Feb. 3, 2000

(30) Foreign Application Priority Data

Mar. 5, 1999 (DE) .......................... 199 09 661

(51) Int. Cl.$^7$ .......................... A61K 7/135; A61K 7/13; D06L 3/00; D06L 3/02; C09B 67/00
(52) U.S. Cl. .................... 424/62; 8/101; 8/102; 8/111; 8/405; 8/406; 8/527; 8/528; 424/401; 424/DIG. 3
(58) Field of Search ..................... 424/401, 62, DIG. 3; 8/405, 406, 527, 528, 101, 102, 111

(56) References Cited

U.S. PATENT DOCUMENTS

| | | | |
|---|---|---|---|
| 4,170,637 A | 10/1979 | Pum | |
| 5,279,313 A | 1/1994 | Clausen et al. | |
| 5,575,989 A | 11/1996 | Caskey | |
| 5,698,186 A | 12/1997 | Weeks | |
| 5,888,484 A | 3/1999 | Schmitt et al. | |
| 5,989,530 A | 11/1999 | Lorenz et al. | |

FOREIGN PATENT DOCUMENTS

| | | |
|---|---|---|
| DE | 38 14 356 A1 | 9/1988 |
| DE | 38 14 356 C2 | 1/1992 |
| DE | 40 26 235 A1 | 2/1992 |
| DE | 40 26 235 | 2/1992 |
| DE | 195 45 853 A1 | 6/1997 |
| DE | 197 23 538 C1 | 9/1998 |
| EP | 0 560 088 A1 | 9/1993 |
| EP | 0 560 088 B1 | 8/1994 |
| GB | 466 172 | 5/1937 |
| WO | 94/16672 | 8/1994 |

OTHER PUBLICATIONS

Roempps Chemie–Lexicon (Chemical Dictionary), Oot–Albrecht, Neumueller, vol. 5, Frankchkh'sche Verlagshaltungs, W. Keller & Co. Stuttgart, 1987, pp. 3845 to 3847.
Roempps Chemie–Lexicon (Chemical Dictionary), Otto–Albrecht, Neumueller, vol. 3, Frasnkchkh'sche Verlagshandlung, W. Keller & Co., Stuttgart, 1987, p. 1653.
Woerterbuch Der Kosmetik by Horst Fey, Wissenschaftliche Verlagsgesellschaft MBH, 1974, p. 363.
International Cosmetic Ingredient Dictionary and Handbook, Eight Edition, 2000, vol. 2, Cosmetic, Toieltry and Fragrance Association, p. 1327.
Product Sheet, Wella Oct. 15, 1993.
Ziolkowsky, Bernd: "Kosmetische Gele: Aufbau und Neuere . . . ", SOFW–Journal, BD. 120, NR. 5, May 1994, pp. 280–284, XP000914570.

*Primary Examiner*—Jose' G. Dees
*Assistant Examiner*—Marina Lamm
(74) *Attorney, Agent, or Firm*—Michael J. Striker

(57) ABSTRACT

The composition for removing or lightening hair color is in the form of a hair color lightening suspension and is mixed with an aqueous oxidizing composition immediately prior to use. The composition includes a combination of from 0.1 to 80 percent by weight of one or more organic lipophilic compounds, namely vegetable or animal fats, vegetable or animal oils, vegetable or animal waxes, paraffin hydrocarbons, higher alcohols or ethers, aliphatic and aromatic esters and/or silicone oils; from 0.1 to 40 percent by weight of at least one lipophilic inorganic or organic thickener, which forms an oleogel and/or lipogel with the lipophilic compounds; from 0.1 to 40 percent by weight of one or more hydrophilic inorganic or organic thickeners; from 10 to 65 percent by weight of at least one inorganic persalt; from 10 to 45 percent by weight of at least one alkaline reacting salt; and auxiliary substances and cosmetic additive ingredients, as needed.

13 Claims, No Drawings

COMPOSITIONS FOR REMOVING OR LIGHTENING HAIR COLOR

BACKGROUND OF THE INVENTION

1. Field of the Invention

The present invention relates to a composition for removing or lightening (bleaching) hair color, especially of human hair, which is obtainable from two components.

2. Prior Art

Usually oxidizing preparations are used for decolorizing or bleaching hair, which are obtained by dissolving a so-called bleaching powder (powder mixture of alkali salts and inorganic persalts, such as sodium or ammonium persulfate) in an aqueous hydrogen peroxide solution.

The use of this kind of bleaching powder, which necessarily comprises a plurality of ingredients, has many disadvantages. The different powder ingredients thus have a tendency to separate during storage or transport because of the use of raw materials having different densities. The heavier ingredients of the powder collect in the lower portion of the powder's container, while the lighter ingredients collect in the upper portion. This un-mixing or separation has the consequence that equal portions of powder taken from different parts of the container have different chemical compositions and thus can have a different decolorizing or bleaching action. In order to prevent this separation it is necessary to shake the powder thoroughly before taking it from the container, which however the user does not usually do. A separation can also be prevented by the use of mixed powders with very small grain size. This however has the disadvantage that those powder mixtures are inclined to generate dust, which lead to irritation of the lungs, especially when the container is opened and the powder removed and mixed with hydrogen peroxide. Furthermore this sort of powder mixture has a large surface area because of its reduced grain size, so that an up-take of moisture occurs on opening and closing of the container and thus a reduction of the decolorizing or hair color lightening action is promoted on account of the deactivation of the oxygen carrier.

The preparation of the ready-to-use mixture occurs by stirring the ingredients in a vessel or by mixing them together in a shaking flask. Especially shaking often involves a troublesome dust development on filling the ingredients into the shaking flask.

There already have been numerous attempts to solve this problem.

Thus, in German Patent Document DE-OS 40 26 235 a mixture comprising a persulfate granulate and a granulate of conventional ingredients of a bleaching agent is described instead of a bleaching powder. Of course the problem of dust generation can be eliminated by use of a granulate, but the problem of separation cannot be solved in this way since it is exceptionally difficult to prepare an individual granulate with identical and constant grain size and batch weight. Furthermore the bleaching or decolorizing action can be impaired because of the differing solubilities of the individual granulate. From an economic standpoint it does not make sense to produce a mixture of several granulates instead of an individual granulate. In EP-PS 0560 088 a powdery agent for lightening or decolorizing the hair is described in which an oil or a liquid wax is added to prevent dust formation. However dust generation cannot be eliminated in this manner. Furthermore a deactivation of the oxygen carrier occurs because of the water content of the powdery raw material employed, whereby the product is unstable and its decolorizing or bleaching action is lost. Furthermore bleaching agents of this type are unsuitable for use in an applicator flask because of their specific gravity and their hydrophobic character, since the powder does not sink to the bottom of the hydrogen peroxide solution and is not sufficiently wet, whereby a non-uniform mixture with a high percentage of undissolved powder is obtained, which clogs the outlet of the applicator flask. The addition of surfactants, which improve the solubility of the powder is similarly problematical, since the storability of the powder is impaired by that.

Pasty two component preparations for making a ready-to-apply pasty preparation for bleaching of human hair are described in DE-OS 38 14 356 and U.S. Pat. 4,170,637. In these preparations the powdery ingredients are worked into a hydrophobic base, comprising oil and wax, so that a paste results. This suspension has the disadvantage that is somewhat inclined toward phase separation, which is noticeable as oil separation. In order to prevent this an absorbing agent, for example silicic acid, is added, whereby the paste again is very solid. In DE-PS 197 23 538 pasty two component preparations were described for making a ready-to-use pasty preparation for bleaching of human hair. This preparation, besides the usual ingredients for bleaching contains a certain thickener combination. This thickener combination comprises an acrylic acid polymer and at least one polymer made from cellulose, alginate and polysaccharide, at least one mineral oil, at least one liquid, long-chain, hydrophobic fatty acid ester and at least one waxy, long-chain, hydrophobic fatty acid ester and/or synthetic beeswax substitutes. These agents are however not satisfactory in every aspect or regard in relation to their behavior at high temperatures.

SUMMARY OF THE INVENTION

It is an object of the present invention to provide a storage-stable, non-dust generating composition for decolorizing hair or lightening or brightening hair color, which is mixed immediately prior to use by simply shaking or stirring with an oxidizing agent preparation and, besides its absolutely dust-free administration and application form, also guarantees very good bleaching action with simultaneously good storage stability between 5 and 45° C., without loosing its outstanding creamy consistency and thus its outstanding decolorizing or bleaching properties when it is cooled and/or heated.

Surprisingly it has now been found that the above-described objects can be attained by using of a pasty decolorizing or hair color lightening composition based on a new special combination of thickening agents and in which addition of emulsifiers is not required.

According to the present invention the composition for removing or brightening or lightening hair color from hair, especially human hair, which is mixed with an aqueous oxidizing agent immediately prior to use and thus present in the form of a hair color lightening or brightening suspension, contains or comprises a combination of (a) from 0.1 to 80 percent by weight of at least one organic lipophilic compound selected from the group consisting of vegetable and animal fats, oils and waxes, paraffin hydrocarbons, higher alcohols and ethers, aliphatic and aromatic esters and silicone oils;.

(b) from 0.1 to 40 percent by weight of at least one inorganic or organic thickener having lipophilic character, that forms an oleogel and/or lipogel with the at least one lipophilic compound;

(c) from 0.1 to 40 percent by weight of at least one inorganic or organic thickener with hydrophilic character;

(d) from 10 to 65 percent by weight of at least one inorganic persalt;

(e) from 10 to 45 percent by weight of at least one alkaline reacting salt; as well as auxiliary substances and additive ingredients as needed.

The suitable organic lipophilic ingredients include, especially, vegetable oils, for example, jojoba oil; petrolatum (Vaseline©);liquid paraffins, especially paraffinum perliquidum and parafiinum subliquidum; silicone oils; liquid, long-chain, hydropobic fatty acid esters, especially octyl palmitate, isocetyl palmitate, isopropyl palmitate and octyl stearate; waxy, long-chain, hydrophobic fatty acid esters and/or synthetic wax replacing substances, such as natural or synthetic beeswax (for example lipowax 6138G® of Lipo Chemicals), $C_{18}$- to $C_{36}$-fatty acids(for example, synchrowax AW1C® of Croda Chemicals Ltd.), $C_{10}$- to $C_{36}$-fatty acid triglycerides, such as octanoic acid/dodecanoic acid-triglycerides, hydrated coconut oil fatty acid glycerides (for example Softisan 100® of Hüls AG), glyceryltribehenate (for example Synchrowax HRC® of Croda ChemicalsLtd.), mixed fatty acid esters (for example Cutina BW® of Henkel KGaA), as well as mixtures of the foregoing ingredients. The use of jojoba oil, fatty acid esters, paraffin oils, combinations of fatty acid esters and paraffin oils as well as combinations of fatty acid esters and/or paraffin oils with Vaseline® is particularly preferred.

The lipophilic compounds are used in a total amount of about 0.1 to 80 percent by weight, preferably from 3 to 65 percent by weight, and especially preferably from 20 to 50 percent by weight, in relation to the total amount of the hair decolorizing or hair color lightening suspension.

Alkali carboxylates, alkaline earth carboxylates or aluminum carboxylates, such as sodium palmitate, aluminum/magnesium hydroxystearate or magnesium stearate, aluminum monostearate, aluminum monodistearate and/or aluminum tristearate; copolymerizates of alkenes, such as ethylene/propylene copolymers; cross-linked organic polymers and lipophilized layered sliicates, such as benzyl dimethylstearyl ammonium hectorite (for example bentone 28 of Fa. Rheox), and mixtures of these compounds are preferred lipophilic thickeners. The use of alkali metal stearates, alkaline earth metal stearates, aluminum stearates and aluminum/magnesium hydroxystearates, and especially magnesium stearates and aluminum stearates, as the lipophilic inorganic or organic thickener component in the composition according to the invention is particularly preferred.

The lipophilic thickeners or their mixtures form an oleogel and/or lipogel when dissolved in the above-described lipoilic compounds. The dissolving of the lipophilic thickeners in the lipophilic component can be assisted by heating or by the use of solvating agents, such as propylene carbonates. Similarly it is possible to use fatty mixtures,of lipophilic thickeners and lipophilic compounds, forexample Brooks Gel® of Fa. Brooks Industries, the Bentone Gel® types of Fa. Rheox, the Myglyol Gel® and Softisan Gel® types of Fa. Hüls AG and Gilugel® types of Fa. BK Giulini Chemie, in which the desired consistency can be individually adjusted by addition of other oils The oleo- and/or lipogel-forming thickeners are used in a total amount of from about 0.1 to 40 percent by weight, preferably from 0.2 to 20 percent by weight, but from 0.5 to 15 percent by weight is especially preferred.

Polymers from the group consisting of cellulose polymer compounds, alginate, polysaccarides and acrylic acid polymers, preferably methyl cellulose compounds, ethyl cellulose compounds, hydroxyethylcellulose compounds, methylhydroxyethylcellulose compounds, methylhydroxypropylcellulose compounds, carboxymethyl cellulose compounds, alginic acids, sodium alginates, ammonium alginates, calcium alginates, gum arabic, guar gum or xanthan gum, or acrylic acid polymers with molecular weights from about 1,250,000 to 4,000,000, alone or in combination with each other, are especially preferred for use as the hydrophilic inorganic or organic thickeners. The use of swelling delaying methylhydroxyethylcelluloses, a combination of alginates with polysaccharides and/or celluloses, or a combination of alginates and/or celluloses with acrylic acid polymers is especially preferred.

The hydrophilic thickeners are used in a total amount of about 0.1 to 40 percent by weight, preferably from 0.2 to 20 percent by weight, and especially preferably in an amount of from 0.5 to 15 percent by weight, in relation to the total amount of hair decolorizing or hair color lightening suspension according to the invention.

Preferably ammonium persulfates and alkali metal persulfates, such as sodium persulfate and potassium persulfate, or mixtures of these inorganic persalts, and alkaline earth peroxides are used as the inorganic persalts. The persalts are used in a total amount of preferably 10 to 65 percent by weight, especially of 20 to 55 percent by weight, in relation to the total amount of the hair decolorizing or hair color lightening suspension.

For example, sodium carbonate, sodium hydrogen carbonate, magnesium carbonate, ammonium carbonate, ammonium hydrogen carbonate, sodium silicate, or a mixture of these salts, are used as the alkali-reacting alkali metal salts or alkaline earth metal salts. These salts are included in the hair decolorizing or hair color lightening composition in a total amount of preferably from 10 to 45 percent by weight, especially preferably from 15 to 35 percent by weight, in relation to the total amount of the hair decolorizing or hair color lightening suspension.

The creamy bleaching agent suspension can also contain standard cosmetic additive ingredients, for example care materials, silicon dioxide, titanium dioxide, chelating agents for heavy metal ions, especially ethylenediaminetetraacetic acid, dyes, especially ultramarine dye stuffs, or perfumes. These cosmetic additive ingredients are used in amounts that are standard for their purposes. For example, the care ingredients, the silicon dioxide and the chelating agents are used in an amount of from 0.01 to 3 percent by weight and the dyes and perfumes are used in an amount of from 0.01 to 2 percent by weight.

The bleaching agent, or hair decolorizing or hair color lightening suspension, preferably contains no surfactant or emulsifier and is water-free. However water content of up to a maximum of 3 percent by weight is allowable.

The hair decolorizing or hair color lightening suspension according to the invention is mixed with an oxidizing preparation immediately prior to use to form an applicable decolorizing paste. This mixing can occur in a dish or by shaking an applicator flask. Particularly an aqueous solution containing hydrogen peroxide or an oil-in-water emulsion (especially a 6 to 12 percent hydrogen peroxide solution or hydrogen peroxide emulsion) can be used as the oxidizing agent preparation. However it is also possible to use an adduct, for example urea peroxide or melamine perhydrate, from which hydrogen peroxide is split off.

The mixture ratio of decolorizing suspension to oxidizing agent preparation is preferably from 2:1 to 1:8, especially from 1:1 to 1:5.

The ready-to-use composition for decolorizing or bleaching of hair obtained after mixing with the oxidizing agent preparation has a pH of about 7.5 to 11, especially from 8 to 9.5.

The ready-to-use composition is applied uniformly on the hair and is rinsed from the hair with water after an acting time of 15 to 60 minutes at room temperature (20 to 25° C.) or from 10 to 50 minutes when the hair is heated (30 to 50° C.).

The creamy bleaching agent suspension can be filled into tubes, sachets or bowls according to its viscosity. Besides the user-friendly product viscosity over a wide temperature range and the easy mixability with the oxidizing agent the composition according to the invention has outstanding storage stability, applicability, distributability and adherence to the hair, as well as a wide range of applications. In comparison to conventional bleaching agents, the composition according to the invention provides an improved lightening or brightening of the hair color shade with a reduced amount of active bleaching ingredient. The decolorizing or lightening composition according to the invention may be very easily rinsed out from the hair with water without leaving a residue because of the emulsifying properties of the gel-forming ingredients.

The following examples illustrate the composition according to the invention, but their details should not be considered as limiting the claims appended hereinbelow.

EXAMPLES

Example 1: Hair Color Brightening or Lightening Composition

| Creamy Hair Color Brightening or Lightening Suspension | |
|---|---|
| 8.0 g | isodecane/ethylene mixed copolymer (Brooks Gel ® of Brooks Industries Inc.) |
| 8.0 g | isopropylpalmitate |
| 16.0 g | jojoba oil |
| 4.0 g | $C_{10}$–$C_{18}$ fatty acid triglycerides (Nesatol ® of Fa.Vevy) |
| 24.2 g | sodium metasilicate |
| 4.0 g | sodium alginate |
| 11.3 g | diammonium persulfate |
| 22.5 g | dipotassium persulfate |
| 1.0 g | zinc stearate |
| 1.0 g | ethylenediaminetetraacetic acid disodium salt |
| 100.0 g | |

First, the liquid ingredients are uniformly mixed with the lipophilic Brooks Gel® (Oleogel) at room temperature to make the creamy bleaching agent suspension and subsequently the premixed solid raw materials are added. Care is taken to provide a uniform distribution of the solid materials in the lipogel matrix.

APPLICATION 25 g of the previously described hair color lightening suspension of example 1 are shaken together with 75 g of a 6 percent hydrogen peroxide solution of the following composition:

| | |
|---|---|
| 6.0 g | hydrogen peroxide |
| 2.0 g | cetyl stearyl alcohol |
| 0.2 g | lanolin alcohol |
| 0.1 g | phosphoric acid (85%) |
| 91.7 g | water |
| 100.0 g | | in an applicator flask for 10 to 15 seconds. Subsequently the decolorizing agent is uniformly distributed on the hair to be lightened by means of an applicator flask. After an acting time of 30 minutes at room temperature (20 to 30° C.) the hair is rinsed with warm water and dried. The brightening or lightening degree amounts to three color shades and can be increased about 1 to 2 color shades by extending the acting time about 20 minutes.

Example 2: Hair Color Brightening or Lightening Composition

| Creamy Hair Color Brightening or Lightening Suspension | |
|---|---|
| 1.9 g | dimethyl distearyl ammonium hectorite (Quaternium-18 Hectorite; Bentone ® 38CE of Rheox Inc.) |
| 34.1 g | octyl stearate |
| 0.5 g | propylene carbonate |
| 23.0 g | disodium persulfate |
| 17.0 g | dipotassium persulfate |
| 20.0 g | sodium metasilicate |
| 1.5 g | xanthane gum |
| 1.5 g | acrylic acid polymer (Synthalene ® K of 3V-Sigma) |
| 0.5 g | ethylenediaminetetraacetic acid disodium salt |
| 100.0 g | |

To make the creamy bleaching agent suspension the organically modified lipophilic layered silicate (Bentone® 38CE) is wet with propylene carbonate, the octyl stearate added and the mixture is subsequently homogenized for 3 minutes with a rotor-stator system at 20,000 rpm at room temperature. The solid premixed raw materials are subsequently added in the lipogel made in this way. Care is taken to provide a uniform distribution of the solid materials in the lipogel matrix.

APPLICATION 25 g of the above described decolorizing agent suspension are stirred uniformly together with 25 g of a 9 percent hydrogen peroxide oil-in-water emulsion of the following composition:

| | |
|---|---|
| 9.0 g | hydrogen peroxide |
| 2.0 g | cetyl stearyl alcohol |
| 0.2 g | lanolin alcohol |
| 0.1 g | phosphoric acid (85%) |
| 88.7 g | water |
| 100.0 g | | in a dish with a brush. Subsequently the pasty decolorizing composition obtained in this manner is applied uniformly to medium brown hair and after an acting time of 30 minutes at room temperature, the hair is rinsed with warm water and dried. The hair treated in this manner is brightened to a bright blond color shade.

Example 3: Hair Color Brightening or Lightening Composition

| Creamy Hair Color Brightening or Lightening Suspension | |
|---|---|
| 40.0 g | octyl stearate |
| 2.5 g | paraffin perliquidum |
| 2.0 g | petrolatum (Vaseline ®) |
| 3.5 g | aluminum tristearate |
| 2.0 g | jojoba oil |
| 4.0 g | disodium persulfate |
| 17.0 g | dipotassium persulfate |
| 8.0 g | diammonium persulfate |
| 18.0 g | sodium metasilicate |
| 2.5 g | sodium alginate |
| 0.5 g | ethylenediaminetetraacetic acid disodium salt |
| 100.0 g | |

First, the aluminum tristearate is completely dissolved in the lipophilic mixture of octyl stearate, paraffin oil and Vaseline® by heating at 110 to 120° C. to make this creamy hair color lightening or brightening suspension. The jojoba oil is uniformly distributed at 70° C. in the cooling oleogel. The premixed solid raw materials are subsequently added to the lipogel arising after cooling to room temperature. Care is taken to provide a uniform distribution of the solid materials in the lipogel matrix.

APPLICATION 25 g of the above described hair color lightening suspension are stirred uniformly together with 37.5 g of a 6 percent hydrogen peroxide solution in a dish with a brush. However it is also possible to provide the hydrogen peroxide solution in an applicator flask and to shake it with the hair color lightening suspension to form a ready-to-use decolorizing composition. The decolorizing composition is then applied uniformly to the hair whose color is to be lightened or brightened and after an acting time of 40 minutes at room temperature it is mixed with water. Then the hair is dried. The degree of hair color lightening amounts to about four color shades or tones.

All percentages, unless otherwise indicated, are percentages by weight.

The disclosure in German Patent Application 199 09 661.9 of Mar. 5, 1999 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in compositions for removing or lightening hair color, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A composition for removing, brightening or bleaching hair color in the form of a hair bleaching suspension, said hair bleaching suspension comprising a combination of from 0.1 to 80 percent by weight of at least one organic lipophilic compound selected from the group consisting of vegetable fats, animal fats, vegetable oils, animal oils, vegetable waxes, animal waxes, paraffin hydrocarbons, higher alcohols, higher ethers, aliphatic esters, aromatic esters and silicone oils;

from 0.1 to 40 percent by weight of at least one inorganic or organic thickener having a lipophilic character and selected from the group consisting of alkaline earth carboxylates, aluminum carboxylates, copolymerizates of alkenes, cross-linked organic polymers and lipophilized layered silicates, whereby an oleogel or lipogel is formed by combining said at least one inorganic or organic thickener together with said at least one organic lipophilic compound;

from 0.1 to 40 percent by weight of at least one organic or inorganic thickener having a hydrophilic character;

from 10 to 65 percent by weight of at least one inorganic persalt;

from 10 to 45 percent by weight of at least one alkaline reacting salt; and auxiliary substances and cosmetic additive ingredients, as needed.

2. The composition as defined in claim 1, wherein said at least one organic lipophilic compound is selected from the group consisting of said vegetable oils, petrolatum, liquid paraffins, said silicone oils, liquid long-chain hydrophobic fatty acid esters, natural beeswax, synthetic beeswax, $C_{18}$- to $C_{36}$-fatty acids, $C_{10}$- to $C_{36}$-fatty acid triglycerides and mixed fatty acid esters.

3. The composition as defined in claim 1, wherein said at least one organic lipophilic compound comprises jojoba oil, at least one fatty acid ester, at least one paraffin oil, a combination of said at least one fatty acid ester and said at least one paraffin oil, a combination of said at least one fatty acid ester and petrolatum, a combination of said at least one fatty acid ester and said at least one paraffin oil and said petrolatum or a combination of said at least one paraffin oil and said petrolatum.

4. The composition as defined in claim 1, wherein said at least one inorganic or organic thickener having said lipophilic character is selected from the group consisting of alkaline earth stearates, aluminum stearates, aluminum/magnesium hydroxystearates and aluminum/magnesium stearates.

5. The composition as defined in claim 1, wherein said at least one inorganic or organic thickener having said lipophilic character is selected from the group consisting of magnesium stearates, aluminum monostearates, aluminum monodistearates, aluminum tristearates, aluminum/magnesium stearates, ethylene/propylene copolymers and benzyl dimethylstearyl ammonium hectorite.

6. The composition as defined in claim 1, wherein said at least one inorganic or organic thickener having said hydrophilic character is selected from the group consisting of cellulose polymers, alginates, polysaccharides and acrylic acid polymers.

7. The composition as defined in claim 1, wherein said at least one inorganic or organic thickener having said hydrophilic character is selected from the group consisting of methyl cellulose compounds, ethyl cellulose compounds, hydroxyethyl cellulose compounds, methylhydroxyethyl cellulose compounds, methylhydroxypropyl cellulose compounds, carboxymethyl cellulose compounds, alginic acid, sodium alginate, ammonium alginate, calcium alginate, arabic gum, xanthan gum and acrylic acid polymers with a molecular weight of from about 1,250,000 to 4,000,000 g/mol.

8. The composition as defined in claim 1, wherein said at least one inorganic persalt is selected from the group consisting of alkaline earth peroxides, alkali metal persulfates and ammonium persulfates.

9. The composition as defined in claim 1, wherein said at least one alkaline reacting salt is selected from the group consisting of sodium carbonate, sodium hydrogen carbonate, magnesium carbonate, ammonium carbonate, ammonium hydrogen carbonate and sodium silicate.

10. The composition as defined in claim 1, containing no surfactant compounds.

11. A ready-to-apply composition for removing, brightening or bleaching hair color made by mixing an aqueous oxidizing composition with a hair bleaching suspension, wherein said aqueous oxidizing composition consists of an aqueous emulsions or solution containing from 6 to 12 percent hydrogen peroxide, and wherein said hair bleaching suspension comprises a combination of from 0.1 to 80 percent by weight of at least one organic lipophilic compound selected from the group consisting of vegetable fats, animal fats, vegetable oils, animal oils, vegetable waxes, animal waxes, paraffin hydrocarbons, higher alcohols, higher ethers, aliphatic esters, aromatic esters and silicone oils; from 0.1 to 40 percent by weight of at least one inorganic or organic thickener having a lipophilic character and selected from the group consisting of alkaline earth carboxylates, aluminum carboxylates, copolymerizates of alkenes, cross-linked organic polymers and lipophilized layered silicates, whereby an oleogel or lipogel is formed by combining said at least one inorganic or organic thickener together with said at least one organic lipophilic compound; from 0.1 to 40 percent by weight of at least one organic or inorganic thickener having a hydrophilic character; from 10 to 65 percent by weight of at least one inorganic persalt; from 10 to 45 percent by weight of at least one alkaline reacting salt; and auxiliary substances and cosmetic additive ingredients, as needed.

12. The ready-to-apply composition as defined in claim 11, wherein said hair bleaching suspension is mixed with said oxidizing composition in a weight ratio of from 2:1 to 1:8.

13. The ready-to-apply composition as defined in claim 11, having a pH from 7.5 to 11.

\* \* \* \* \*